(12) United States Patent
Schmidt

(10) Patent No.: US 6,348,434 B1
(45) Date of Patent: Feb. 19, 2002

(54) HERBICIDAL EMULSIFIABLE CONCENTRATE

(75) Inventor: Friedrich Schmidt, Engelstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/346,157

(22) Filed: Jul. 1, 1999

(51) Int. Cl.$^7$ ............................................. A01N 63/00
(52) U.S. Cl. ...................................................... 504/116.1
(58) Field of Search ................................. 504/130, 116

(56) References Cited

U.S. PATENT DOCUMENTS

| | | | |
|---|---|---|---|
| 5,384,305 A | 1/1995 | Foster et al. ................. | 504/130 |
| 5,674,807 A | * 10/1997 | Baltruschat ................. | 504/130 |

FOREIGN PATENT DOCUMENTS

| WO | WO 98/48624 | 3/1998 |
|---|---|---|

OTHER PUBLICATIONS

U.S. application No. 09/240,418, filed Jan. 29, 1999.

\* cited by examiner

Primary Examiner—Jose' G. Dees
Assistant Examiner—Konata M. George
(74) Attorney, Agent, or Firm—Barbara V. Maurer

(57) ABSTRACT

The invention relates to a non-aqueous, emulsifiable concentrate (EC) formulation for herbicidal crop protection active compounds which consists essentially of (a) 25 to 150 g/L of at least one fluorinated herbicidal compound,
(b) 400 to 900 g/L of one or more herbicidal alkyl phenoxyalkanoates,
(c) 10 to 100 g/L of at least one non-ionic surfactant,
(d) 10 to 100 g/L of at least one benzene sulfonate,
(e) 50 to 600 g/L of one or more solvent selected from the group consisting of aliphatic or aromatic hydrocarbons, methylated plant oils and water-miscible polar aprotic organic solvents, and
(f) optionally, up to 5 g/L of at least one defoamer, and to the use of such a emulsifiable concentrate as a herbicide.

9 Claims, No Drawings

HERBICIDAL EMULSIFIABLE CONCENTRATE

BACKGROUND OF THE INVENTION

Emulsifiable concentrate (EC) formulations are favored liquid delivery systems for agriculturally active compounds. As a rule, conventional ECs contain an active ingredient, one or more surfactants which act as emulsifiers upon dilution of the EC with water, and a water immiscible solvent. Typical solvents for conventional EC formulations are aliphatic or aromatic hydrocarbons, as for example, xylene, Shellsol A or Solvesso 200. These solvents have very low solubilities in water and are capable of dissolving a wide range of active ingredients.

Due to the presence of the solvent, many pesticides formulated as an EC have advantages such as a higher degree of systemicity and higher overall activity compared to the same pesticide formulated as a wettable powder (WP), water dispersible granule (WG) or suspension concentrate (SC).

Such concentrates are easy to store and transport and various adjuvants may be added to increase the efficacy of the formulation. A good EC, however, requires that a stable emulsion is formed upon dilution with water, which emulsion does not separate upon standing. Furthermore, there should not be any crystallization of the active from the EC after water dilution. In addition, the EC itself has to be physico-chemically stable during extended storage periods and under widely varying storage temperatures.

International Patent Application WO 98/48624 suggests the improvement of the emulsion stability of ECs containing low amounts of a water-insoluble fluorinated active agricultural ingredients which optionally contains a diluent active agricultural ingredient, by using a comparably high amount of a water-insoluble $C_6$–$C_1$ alkyl pyrrolidone. However, the $C_6$–$C_{18}$ alkyl pyrrolidones are highly corrosive and too expensive to be used in a broad range herbicidal product for common use.

Moreover, WO 98/48624, preferably uses an ethoxylated nonyl phenol phosphate ester as an anionic surfactant. These surfactants may damage the environment due to their capability to form toxic metabolites and their use is not favored due to their suspected estrogenic activity.

Accordingly, it is an object of the present invention to provide novel, herbicidal ECs.

It is a further object of this invention to provide a stable, effective emulsifiable concentrate (EC) containing low amounts of at least one fluorinated herbicidal compound with high amounts of one or more herbicidal alkyl phenoxyacetates acting as a diluent which do not have the disadvantages of the ECs of the art.

It is also an object of the invention to provide methods for controlling undesired weed by contacting plants with a herbicidally effective amount of these EC formations upon dilution with water.

It is another object of the invention to provide selective herbicidal compositions obtainable by emulsifying the new ECs in water.

These and other objects and features of the invention will be more apparent from the detailed description set forth hereinbelow, and from the appended claims.

SUMMARY OF THE INVENTION

The present invention provides a novel stable, non-aqueous emulsifiable concentrate (EC) for herbicidally active compounds which consists essentially of (a) 25 to 150 g/L of at least one fluorinated herbicidal compound, (b) 400 to 900 g/L of one or more herbicidal alkyl phenoxyalkanoates, (c) 10 to 100 g/L of at least one non-ionic surfactant, (d) 10 to 100 g/L of at least one benzene sulfonate, (e) 50 to 600 g/L of one or more solvents selected from the group consisting of aliphatic or aromatic hydrocarbons, methylated plant oils and water-miscible polar aprotic organic solvents, and (f) optionally, up to 5 g/L of at least one defoamer:

These new emulsifiable concentrate formulations exhibit excellent selective herbicidal activity in various crops.

DETAILED DESCRIPTION OF THE PREFERRED EMBODIMENTS

It has surprisingly been found that the EC formulations consisting essentially of (a) 25 to 150 g/L of at least one fluorinated herbicidal compound, (b) 400 to 900 g/L of one or more herbicidal alkyl phenoxyalkanoates, (c) 10 to 100 g/L of at least one non-ionic surfactant, (d) 10 to 100 g/L of at least one benzene sulfonate, (e) 50 to 600 g/L of one or more solvent selected from the group consisting of aliphatic or aromatic hydrocarbons, methylated plant oils and water-miscible polar aprotic organic solvents, and (f) optionally, up to 5 g/L of at least one defoamer;

exhibit high physicochemical stability and excellent application properties.

As used herein in the new EC formulations, a "herbicidal compound" is a synthetic compound which has the capability of control undesired weeds in crops; and a "fluorinated herbicidal compound" is a synthetic compound which is substituted by at least one fluorine atom which has the capability of control undesired weeds in crops.

Suitable fluorinated herbicidal compounds are those which are solid at room temperature and are substantially insoluble in water, but soluble in an organic solvent.

Preferred fluorinated herbicides (a) are the compounds selected from the group consisting of:

acifluorfen, carfentrazone-ethyl, clodinafop-propargyl, diflufenican, dithiopyr, ethoxyfen-ethyl, flamprop-M-isopropyl, flamprop-M-methyl, flazasulfuron, fluazifop, fluchloralin, flufenacet (BAY FOE 5043 or fluthiamid), flumetsulam, flumioxazin, fluometuron, fluoroglycofen, flupoxam, fluridone, fluroxypyr, flurprimidol, flurtamone, fluthiacet-methyl, fomesafen, haloxyfop, isoxaflutole, lactofen, norflurazon, oxyfluorfen, picolinafen, propachlor, sulfentrazone, thiazopyr and trifluralin.

Most of these herbicidal compounds are described in "The Pesticide Manual," 11th Edition, The British Crop Protection Council and The Royal Society of Chemistry, 1997, (hereinbelow abbreviated as "Pesticide Manual").

Preferred for use in the present invention are the fluorinated herbicidal compounds of formula I

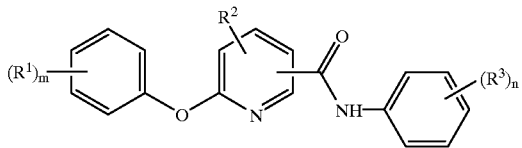

(I)

in which
R[1] and R[3] each independently represent a fluorine atom or a fluoroalkyl, preferably a $C_1$–$C_6$ fluoroalkyl group, in particular a trifluoromethyl group;
R[2] represents a hydrogen atom or an optionally substituted alkyl or alkoxy group; and
m and n each independently represent an integer from 1 to 2.

Particularly preferred herbicidal compounds (a) are the picolinamides disclosed by EP-A-0 447 004, in particular those of formula I1

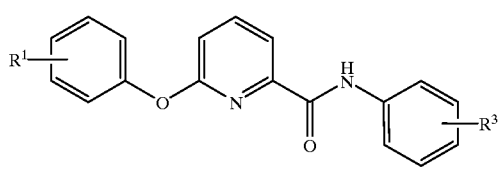

(I1)

wherein R[1] and R3 are as described for formula I.

An especially preferred compound for use in the present invention is N-(4-fluorophenyl)-2-(3-α,α,α-trifluoromethylphenoxy)-6-pyridinecarboxamide, also known as picolinafen.

The new ECs contain at least one fluorinated herbicide (a) and at least one herbicidal alkyl phenoxyacetate (b).

The herbicidal compounds can be, for example, compounds which possess a high herbicidal activity within a wide concentration range and/or at low dosages, and may be used in agriculture, in particular, for the selective control of undesired plants such as *Alopecurus myosuroides, Echinochloa crus-galli, Setaria viridis, Galium aparne, Stellaria media, Veronica persica, Lamium purpureum, Viola arvensis, Abutilon theophrasti, Ipomoea purpurea* and *Amaranthus retroflexus* by pre- and post-emergence application, particularly in certain crops such as maize and rice.

Suitable herbicidal alkyl phenoxyalkanoates (b) are those which are liquid at room temperature and substantially insoluble in water, but soluble in an organic solvent.

Preferred alkyl phenoxyalkanoates are esters of 2-phenoxyacetic or 2-phenoxypropionic acid having a straight chained or branched $C_2$–$C_{12}$ alkyl, in particular a branched $C_4$–$C_{10}$ alkyl group. Most preferred are the 2-ethylhexyl esters.

Particularly preferred are the compounds of formula II

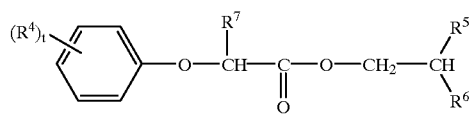

(II)

in which
R[4] each independently represents a halogen atom or a $C_{1-6}$ alkyl group,
R[5] and R[6] each independently represent a $C_{1-6}$ alkyl group,
R[7] represents a hydrogen atom or a methyl group, and
t represents an integer from 1 to 3.

Most preferred are the compounds selected from the group consisting of: 2-ethylhexyl(4-chloro-2-methylphenoxy)-acetate [also known as MCPA-2EH], 2-ethylhexyl(2,4-dichlorophenoxy)-acetate [also know as 2,4-D-2EH] and 2-ethylhexyl 2-(4-chloro-2-methylphenoxy) propionate [also known as mecoprop-2EH] or mixtures thereof.

Mixtures of the above mentioned herbicides or mixtures of herbicides with other active ingredients like fungicides, insecticides, acaricides and nematicides are possible.

Suitable non-ionic surfactants (c) are preferably polyglycolether derivatives of aliphatic alcohols and saturated or non-saturated fatty acids, which have 3 to 20 glycol ether groups and 8 to 20 carbon atoms in the (aliphatic) hydrocarbon residue. Other suitable non-ionic surfactants are 20 to 250 ethylene glycol ether groups containing polyadducts of ethylene oxide and propylene oxide, ethylene diamino polypropylene glycol and alkyl polypropylene glycol with 1 to 10 carbon atoms in the alkyl moiety. The substances normally contain 1 to 5 ethylene glycol units per propylene glycol unit. Examples of non-ionic surfactants are castor oil polyglycol ethers, polyadducts of ethylene oxide and propylene oxide, tributyl phenoxy polyethoxy ethanol and tristyrylphenol ethoxylates.

Preferred are ethoxylatedeils such a castor or canola oil ethoxylates having at least 25, preferably 27 to 37 ethoxy units, such as Sunaptol® CA350 (castor oil ethoxylate with about 35 ethoxy units) of Uniqema (formerly ICI Surfactants), Mergital® EL33 (castor oil ethoxylate with about 33 ethoxy units) of Henkel KGaA, Eumulgin® CO3373 (canola oil ethoxylate with about 30 ethoxy units) of Henkel KGaA and Ukanil® 2507 (castor oil ethoxylate with about 32 ethoxy units) of Uniqema.

Another group of preferred nonionic surfactants (c) are alcohol alkoxylates, which are based on alkoxy units having 2 carbon atoms, thus being a mixed ethoxylate, or 2 and 3 carbon atoms, thus being a mixed ethoxylate/propoxylate. In a preferred aliphatic alcohol alkoxylate, the alkoxylate chain may have at least 5 alkoxy moieties, suitably from 5 to 25 alkoxy moieties, preferably 5 to 15, in particular 5 to 11. The alcohol moiety is as a rule derived from a $C_{9-18}$ aliphatic alcohol. Preferred alcohols are typically 50 wt.-% straight-chained and 50 wt.-% branched alcohols.

Particularly preferred surfactants are the Synperonic® alcohol ethoxylates from Uniqema, in particular, Synperonic® 91-6.

Furthermore preferred alcohol alkoxylates are mono-branched alcohol ethoxylates such as Atplus® MBA 11-7 (branched $C_{11}$ alcohol ethoxylate with 7 ethoxy units) of Uniqema or Genapol® X-60 (alcohol ethoxylate with 6 ethoxy units) of Clariant.

Suitable alkyl benzene sulfonates (d) are, for example, the sodium, calcium or triethyl ammonium salts of alkyl benzene sulfonic acid. Most preferred alkyl benzene sulfonates (d) are the sodium, calcium or triethyl ammonium salts of dodecyl benzene sulfonic acid, in particular Rhodacal® 70/B (70% calcium dodecyl benzene sulfonate in n-butanol), Rhodacal® 60/BE (60% calcium dodecyl benzene sulfonate in 2-ethylhexanol) and Rhodacal® 2283 (70% ammonium dodecyl benzene sulfonate) all of Rhodia GmbH (formerly Rhô ne-Poulenc), Phenylsulfonat CA 100 (40% calcium dodecyl benzene sulfonate in Genopol X-060 and Solvesso 200) of Clariant GmbH (formerly Hoechst AG) or Nansa®

EVM 70/2E (57% linear dodecyl benzene sulfonate in 2-ethylhexanol) of Albright & Wilson.

The surfactants (c) and (d) provide good emulsifying properties without containing alkylphenol ethoxylates such as Synperonic® NP9 and/or the anionic derivatives thereof, for example, ethoxylated alkylaryl phosphate esters such as Rhodofac® RE 610. Alkylphenol ethoxylates and their derivatives may damage the environment due to their capability to forming toxic metabolites and their suspected estrogenic activity.

Suitable solvents (e) are non-polar water-immiscible solvents or polar aprotic water miscible organic solvents. The non-polar solvents are selected from the group consisting of aliphatic or aromatic hydrocarbons and esters of plant oils or mixtures thereof.

Aliphatic and aromatic hydrocarbons such as hexane, cyclohexane, benzene, toluene, xylene, mineral oil or kerosin or substituted naphthalenes, mixtures of mono- and polyalkylated aromatics are, for example, commercially available under the registered trademarks Solvesso®, Shellsol®, Petrol Spezial® and Exxsol®.

Esters of plant oils, which are used as nonpolar, water-immiscible solvents according to the present invention are, as a rule, alkyl esters obtainable from medium chained fatty acids by esterification with alkanols or by transesterification of the corresponding plant oils preferably in the presence of a lipase. Preferred fatty acids of these plant oils have 5 to 20, in particular 6 to 15 carbon atoms. In a preferred embodiment, the methyl ester of the plant oil used is the methyl ester of caprylic/capric ester or of capric ester having a distribution of fatty acid chain lenghts around 10 units.

Particularly preferred methyl esters of plant oils are Witconol® 1095 and Witconol® 2309 which are commercially available from the Witco Corporation, Houston, USA.

The water-miscible polar aprotic organic solvents are preferably compounds which exhibit a dielectric constant of 2.5 or more at 25° C., in particular from 2.7 to 4.0 at 25° C. Particularly preferred are cyclic amides and lactones as for example N-methylpyrrolidone, N-cyclohexylpyrrolidone and γ-butyrolactone, most preferred are γ-butyrolactone and N-methylpyrrolidone or mixtures thereof.

Also preferred are water-miscible polar aprotic solvents selected from the group consisting of alkyl lactates, in particular, isopropyl lactate such as Plurasolv® IPL which is obtainable from Plurac, alkyl carbonates, polyethylene glycols, polyethylene glycol alkyl ethers, polypropylene glycols and polypropylene glycol alkyl ethers, and most preferably particular isopropyl lactate, or mixtures thereof.

Suitable defoamers (f) are siloxan derivatives or perfluoroalkylphosphonic/perfluoroalkylphosphinc acids, in particular polydimethylsiloxanes, such as Rhodorsil® 416 or Rhodorsil® 454 from Rhodia or mixtures comprising perfluoro-($C_{6-18}$)-alkylphosphonic acids and perfluoro-($C_{6-18}$)-alkylphosphinic acids, such as Fluowet® PL80, Fluowet® PP from Clariant.

Preferred embodiments of the invention are EC formulations which consist essentially of:

(a) 30 to 125 g/L, in particular 40 to 110 g/L, of at least one fluorinated herbicidal compound of formula 1, in particular, a compound of formula I1, most preferred picolinafen;

(b) 700 to 875 g/L, in particular 750 to 850 g/L, of one or more herbicidal alkyl phenoxyalkanoates of formula II, most preferred 2,4-D-2EH, MCPA-2EH or mecoprop-2EH;

(c) 20 to 75 g/L, in particular 40 to 70 g/L, of at least one non-ionic surfactant, in particular, of at least one ethoxylated castor oil;

(d) 20 to 75 g/L, in particular 40 to 70 g/L, of at least one sodium or calcium alkyl-benzene sulfonate;

(e) 50 to 200 g/L, in particular 60 to 150 g/L, of one or more solvents selected from the group consisting of aliphatic or aromatic hydrocarbons, methyl $C_{8-12}$ carboxylates, N-methylpyrrolidone, γ-butyrolactone and isopropyl lactate; and (f) optionally up to 2 g/L of at least one defoamer selected from the group consisting of polydimethylsiloxanes and perfluoroalkylphosphonic/perfluoroalkylphosphinc acids:

Another aspect of the invention is a process for the preparation of an EC as described hereinbefore, which comprises mixing all the components in a dissolver.

Furthermore, the invention relates to a method of combating pests at a locus which comprises treating the locus with a composition obtained from emulsifying an EC according to the invention in water. Moreover, the invention relates to the use of an EC according to the invention as a pesticide.

As commodities, the inventive pesticidal ECs of the present invention are preferably be in a concentrated form whereas the end-user generally employs diluted compositions. Said compositions may be diluted to concentrations down to 0.001% of active ingredient (a.i.). The doses usually are in the range of about 0.01 to 10 kg a.i./ha.

The said compositions may also comprise other auxiliaries such as chemical stabilizers, viscosity controlling agents, thickeners, adhesives, fertilizers, or other active pesticide ingredients to obtain special effects.

The ECs according to this invention exhibit a high physicochemical stability despite the high concentrations of the herbicidally active ingredients (a) and (b). The emulsions obtained with these ECs upon dilution with water are surprisingly stable, although they do not contain any additional $C_6$–$C_{18}$ alkyl pyrrolidones.

For a clearer understanding of the invention, specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims.

PREPARATION EXAMPLES

The registered trademarks and other designations denote the following products:

| Ingredient | Composition | Manufacturer |
| --- | --- | --- |
| AgsolEx ® 1 | N-methylpyrrolidone- | ISP |
| AgsolEx ® BLO | γ-butyrolacton | ISP |
| Atlox ® 4855B | Blend of calcium alkylarylsulfonate and nonionic surfactant in an aromatic solvent | Uniqema |
| Exxsol ® D110 | Aliphatic hydrocarbon mixture | Exxon Chemicals |

-continued

| Ingredient | Composition | Manufacturer |
| --- | --- | --- |
| Fluowet ® PL80 | Mixture of 80% perfluorinated phophinic/phosphoric acids and 20% water | Clariant |
| Plurasolv ® IPL | Isopropyl lactate | Plurac |
| Rhodacal ® 70/B | 70% Calcium dodecyl benzene sulfonate | Rhodia |
| Rhodacal ® 60/BE | 60% Calcium dodecyl benzene sulfonate | Rhodia |
| Rhodorsil ® 454 | Mixture of polydimethylsiloxanes and silica | Rhodia |
| Solvesso 200 | Aromatic hydrocarbon mixture | Exxon Chemicals |
| Ukanil ® 2507 | Castor oil ethoxylate | Uniqema |
| Witcono ® 1095 | Technical methyl decanoate | Witco Corp. |

Examples 1 to 3

EC formulations are prepared containing:

| | | Concentration (g/L) Example | | |
| --- | --- | --- | --- | --- |
| Component | Function | 1 | 2 | 3 |
| Picolinafen | Active Ingredient (a) | 50 | 50 | 50 |
| MCPA 2-EH | Active Ingredient (b) | 780 | 780 | 780 |
| Atlox 4855 B | Emulsifying system (c) + (d) | 100 | 100 | 100 |
| Fluowet PL 80 | Defoamer (f) | 0.5 | 0.5 | 0.5 |
| Solvesso 200 | Solvent (e) | To 1 L | — | — |
| Purasolv IPL | Solvent (e) | — | to 1 L | — |
| Exxsol D 110 | Solvent (e) | — | — | to 1 L |

Foamimg Behavior

The foaming behavior is assessed according to CIPAC Method MT 47 and is shown in the following Table I.

TABLE I

| | Foaming behavior | | |
| --- | --- | --- | --- |
| Test | Example 1 | Example 2 | Example 3 |
| Persistant Foaming (2% in CIPAC Standard Water C) | | | |
| after 10 s | 7.5 mL | 10 mL | 2.5 mL |
| after 1 minutes | 0 mL | 0 mL | 0 mL |
| after 3 minutes | 0 mL | 0 mL | 0 mL |
| after 12 minutes | 0 mL | 0 mL | 0 mL |

The properties of the EC formulations have been evaluated according to the following CIPAC procedures:

(A) Emulsion Characterisitics (CIPAC MT 36)

5 mL of the respective EC are mixed with water (342 ppm hardness) to give 100 mL of an aqueous emulsion. The stability of the emulsion is assessed in terms of oil or cream which separates while the emulsion is allowed to stand undisturbed for 24 hours at 30° C. The ability to re-emulsify at the end of the 24 hours period is also determined (B) Low Temperature Stability (CIPAC MT 39)

A sample of the respective EC is maintained for 1 hour at 0° C. and the volume of any separated solid or oily matter is then recorded. Storage at 0° C. is continued for 7 days. Thereupon the sample is allowed to remain undisturbed at ambient temperature for 3 hours. Subsequently, the sample is centrifuged and any solid matter and the volume thereof is recorded.

The spray dilutions of the formulations proved to be homogeneous emulsions which were entirely stable over at least 2 hours at 30° C. (CIPAC Method MT 36). The formulations exposed no precipitation of solid material when they where stored over a period of 7 days at 0° C. (CIPAC Method MT 39).

Examples 4 to 6

EC formulations are prepared containing:

| | | Concentration (g/L) Example | | |
| --- | --- | --- | --- | --- |
| Component | Function | 4 | 5 | 6 |
| Picolinafen | Active Ingredient (a) | 50 | 50 | 50 |
| MCPA 2-EH | Active Ingredient (b) | 780 | 780 | 780 |
| Ukanil 2507 | Nonionic surfactant (c) | 60 | — | 50 |
| Rhodacal 60/BE | Anionic surfactant (d) | 60 | — | — |
| Rhodacal 70/B | Anionic surfactant (d) | — | — | 50 |
| Atlox 4855 B | Emulsifying system (c) + (d) | — | 100 | — |
| Rhodorsil 454 | Defoamer (f) | — | 0.5 | — |
| Exxsol D 110 | Solvent (e) | to 1 L | — | — |
| Solvesso 200 | Solvent (e) | — | to 1 L | — |
| Witconol 1095 | Solvent (e) | — | — | to 1 L |

The properties of the EC formulations have been evaluated according to the following CIPAC or OECD procedures:

(C) pH 1% in water (CIPAC MT 75)

The pH of a 1% dilution of the formulation in demineralized water is determined at 20° C. by means of a pH meter and a glass electrode.

(D) Density (OECD Guideline 109)

The density of the respective EC is measured at 20° C. by means of an oscillating density meter.

The characteristics of the EC formulations of examples 4 to 6 obtained with the methods described hereinabove are shown in the following Table II.

TABLE II

| | Characteristics of the EC formulations | | | |
| --- | --- | --- | --- | --- |
| Characteristic | Test Method | Example 4 | Example 5 | Example 6 |
| Emulsion Characteristics | CIPAC MT 36 | | | |
| after 30 min | | uniform | uniform | uniform |
| after 2 h | | uniform | uniform | uniform |
| after 24 h | | uniform | uniform | uniform |
| re-emulsification | | uniform | uniform | uniform |
| final emulsion stability | | uniform | uniform | uniform |
| Low temperature stability at 0° C. | CIPAC MT 39 | no separated material | no separated material | no separated material |
| pH 1% in water | CIPAC MT 75 | 4.4 | not det. | not det. |
| Density | OECD 109 | 1.048 g/mL | 1.066 g/mL | 1.052 g/mL |

The foaming behavior of all EC formulations had been assessed according to CIPAC Method MT 47. There was less than 20 ml of persistent foam upon dilution with water (1 to 2%) and 30 inversions in a 100 ml graduated cylinder filled with 100 ml water.

Examples 7 to 9

EC formulations are prepared containing:

| Component | Function | Concentration (g/L) Example 7 | 8 | 9 |
|---|---|---|---|---|
| Picolinafen | Active Ingredient (a) | 50 | 100 | 100 |
| 2,4-D 2-EH | Active Ingredient (b) | 422 | 844 | 844 |
| Ukanil 2507 | Nonionic surfactant (c) | 60 | 60 | 60 |
| Rhodacal 60/BE | Anionic surfactant (d) | 60 | 60 | 60 |
| AgsolEx BLO | Solvent (e) | to 1 L | to 1 L | — |
| AgsolEx1 | Solvent (e) | — | — | to 1 L |

The characteristics of the EC formulations of examples 7 to 9 obtained with the methods described hereinabove are shown in the following Table III.

TABLE III

Characteristics of the EC formulations

| Characteristic | Test Method | Example 7 | Example 8 | Example 9 |
|---|---|---|---|---|
| Emulsion Characteristics | CIPAC MT 36 | | | |
| after 30 minutes | | uniform | Uniform | uniform |
| after 2 hours | | uniform | uniform | uniform |
| after 24 hours | | uniform | uniform | uniform |
| re-emulsification | | uniform | uniform | 0.5 ml oil |
| final emulsion stability | | uniform | uniform | uniform |
| Low temperature stability at 0° C. | CIPAC MT 39 | no separated material | no separated material | no separated material |
| pH 1% in water | CIPAC MT 75 | 6.4 | 6.2 | not det. |
| Density | OECD 109 | 1.133 g/mL | 1.141 g/mL | not det. |

The spray dilutions (emulsions) of examples 7 to 9 are stable despite the presence of water-miscible substances (N-methylpyrrolidone, γ-butyrolactone). The ingredients have a good environmental profile. The foaming behavior of all EC formulations had been assessed according to CIPAC Method MT 47. There was less than 20 ml of persistent foam upon dilution with water (1 to 2%) and 30 inversions in a 100 ml graduated cylinder filled with 100 ml water.

What is claimed is:

1. A non-aqueous, emulsifiable concentrate formulation (EC) for herbicidal crop protection active compounds which consists essentially of
   (a) 25 to 150 g/L of at least one fluorinated herbicidal compound;
   (b) 400 to 900 g/L of one or more herbicidal alkyl phenoxyalkanoates,
   (c) 10 to 100 g/L of at least one non-ionic surfactant,
   (d) 10 to 100 g/L of at least one benzene sulfonate,
   (e) 50 to 600 g/L of one or more solvent selected from the group consisting of aliphatic or aromatic hydrocarbons, methylated plant oils and water-miscible polar aprotic organic solvents, and
   (f) optionally, up to 5 g/L of a defoamer.

2. A non-aqueous, emulsifiable concentrate formulation (EC) of claim 1 wherein the fluorinated herbicidal compound (a) is of the formula

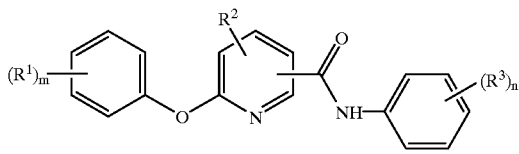

in which
   $R^1$ and $R^3$ each independently represent a fluorine atom or a fluoroalkyl, group;
   $R^2$ represents a hydrogen atom or an optionally substituted alkyl or alkoxy group;
   m and n each independently represent an integer from 1 to 2.

3. An emulsifiable concentration formation claim 1 wherein said fluorinated herbicidal compound (a) is N-(4-fluorophenyl)-2-(3-α,α,α-trifluoromethylphenoxy)-6-pyridinecarboxamide.

4. An emulsifiable concentration formation in accordance with claim 1 wherein the herbicidal allayl phenoxyalkanoate (b) is an alkyl phenoxy acetate of formula II

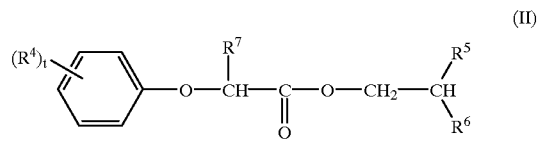

wherein
   $R^4$ each independently represents a halogen atom or a $C_{1-6}$ alkyl group,
   $R^5$ and $R^6$ each independently represent a $C_{1-6}$ alkyl group,
   $R^7$ represents a hydrogen atom or a methyl group, and
   t represents an integer from 1 to 3.

5. An emulsifiable concentration formation claim 4 wherein the alkyl phenoxy acetate (b) is selected from the group consisting of 2-ethylhexyl(4-chloro-2-methylphenoxy)-acetate, 2-ethylhexyl(2,4-dichlorophenoxy)-acetate and 2-ethylhexyl 2-(4-chloro-2-methylphenoxy)-propionate or a mixture thereof.

6. An emulsifiable concentration formation claim 1 wherein said non-ionic surfactant (c) is an ethoxylated castor oil.

7. An emulsifiable concentration formation claim 1 wherein said benzene sulfonate (d) is a sodium or calcium alkyl-benzene sulfonate.

8. An emulsifiable concentration formation claim 1 which consists essentially of
   (a) 30 to 125 g/L of at least one fluorinated herbicidal compound of formula I;
   (b) 700 to 875 g/L of one or more herbicidal alkyl phenoxyalkanoate of formula II,
   (c) 20 to 75 g/L of at least one non-ionic surfactant,
   (d) 20 to 75 g/L of at least one sodium or calcium alkyl-benzene sulfonate,
   (e) 50 to 200 g/L of one or more solvent selected from the group consisting of aliphatic or aromatic hydrocarbons, methyl $C_{8-12}$ carboxylates, N-methylpyrrolidone, γ-butyrolactone and isopropyl lactate; and (f) optionally, up to 2 g/L of at least one defoamer selected from the group consisting of polydimethylsiloxanes and perfluoroalkylphosphonic/perfluoroalkylphosphinc acids.

9. A method for the control of undesired weed at a locus which comprises emulsifying the formulation of claim 1 with water and treating said locus with the obtained dined aqueous formulation.

* * * * *